(12) United States Patent
Jeon et al.

(10) Patent No.: US 11,987,659 B2
(45) Date of Patent: May 21, 2024

(54) HYDROGENATION REACTION CATALYST AND PREPARATION METHOD THEREFOR

(71) Applicant: HANWHA SOLUTIONS CORPORATION, Seoul (KR)

(72) Inventors: Bong Sik Jeon, Daejeon (KR); Wan Jae Myeong, Daejeon (KR); Woo Jin Park, Seongnam-si (KR); Eui Geun Jung, Seoul (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 501 days.

(21) Appl. No.: 16/956,929

(22) PCT Filed: Dec. 20, 2018

(86) PCT No.: PCT/KR2018/016310
§ 371 (c)(1),
(2) Date: Jun. 22, 2020

(87) PCT Pub. No.: WO2019/132407
PCT Pub. Date: Jul. 4, 2019

(65) Prior Publication Data
US 2021/0002403 A1    Jan. 7, 2021

(30) Foreign Application Priority Data

Dec. 29, 2017   (KR) .................. 10-2017-0183458

(51) Int. Cl.
| | | |
|---|---|---|
| *B01J 35/30* | (2024.01) | |
| *B01J 21/08* | (2006.01) | |
| *B01J 23/72* | (2006.01) | |
| *B01J 23/755* | (2006.01) | |
| *C08F 240/00* | (2006.01) | |
| *B01J 27/02* | (2006.01) | |

(52) U.S. Cl.
CPC ............ *C08F 240/00* (2013.01); *B01J 21/08* (2013.01); *B01J 23/72* (2013.01); *B01J 23/755* (2013.01); *B01J 35/30* (2024.01); *B01J 27/02* (2013.01); *B01J 35/393* (2024.01)

(58) Field of Classification Search
CPC ................................ B01J 35/002; B01J 35/30
See application file for complete search history.

(56) References Cited

U.S. PATENT DOCUMENTS

| | | | |
|---|---|---|---|
| 3,687,989 A | 8/1972 | Blates | |
| 3,859,370 A * | 1/1975 | Carter ................... | C07C 29/141 208/143 |
| 3,865,716 A * | 2/1975 | Sosnowski ............. | B01J 29/061 208/143 |
| 4,251,672 A * | 2/1981 | Carter ................... | C07C 29/175 585/269 |
| 4,328,090 A | 5/1982 | Stuckey, Jr. et al. | |
| 4,650,563 A | 3/1987 | Jacobson et al. | |
| 4,952,639 A | 8/1990 | Minomiya et al. | |
| 5,223,470 A * | 6/1993 | Bouwman .............. | B01J 23/755 502/222 |
| 5,648,577 A | 7/1997 | Ho et al. | |
| 5,728,644 A | 3/1998 | Ho et al. | |
| 5,831,138 A | 11/1998 | Ho et al. | |
| 6,124,514 A * | 9/2000 | Emmrich ............... | C10G 21/00 208/143 |
| 6,281,163 B1 * | 8/2001 | Van Dijk ............... | B01J 23/755 554/146 |
| 7,396,799 B2 | 7/2008 | Chen et al. | |
| 7,678,730 B2 | 3/2010 | Mironov et al. | |
| 7,678,731 B2 | 3/2010 | Mironov et al. | |
| 7,678,732 B2 | 3/2010 | Chen et al. | |
| 7,737,072 B2 | 6/2010 | Mironov et al. | |
| 7,737,073 B2 | 6/2010 | Mironov et al. | |
| 7,754,645 B2 | 7/2010 | Kuperman et al. | |
| 7,947,623 B2 | 5/2011 | Mironov et al. | |
| 8,329,610 B2 | 12/2012 | Gao et al. | |
| 2006/0058174 A1 | 3/2006 | Chen et al. | |
| 2007/0179055 A1 | 8/2007 | Chen et al. | |
| 2008/0305947 A1 | 12/2008 | Chen et al. | |
| 2009/0011931 A1 | 1/2009 | Chen et al. | |
| 2009/0054225 A1 | 2/2009 | Mironov et al. | |
| 2009/0054226 A1 | 2/2009 | Mironov et al. | |
| 2009/0057201 A1 | 3/2009 | Brait et al. | |
| 2009/0107891 A1 | 4/2009 | Kuperman et al. | |
| 2009/0200204 A1 | 8/2009 | Mironov et al. | |
| 2009/0308790 A1 | 12/2009 | Gao et al. | |
| 2010/0234212 A1 | 9/2010 | Brait et al. | |
| 2020/0369794 A1 | 11/2020 | Seo et al. | |
| 2022/0023842 A1 * | 1/2022 | Park ........................ | B01J 37/009 |
| 2022/0362749 A1 * | 11/2022 | Park ........................ | B01J 37/088 |
| 2022/0362750 A1 * | 11/2022 | Park ........................ | C08F 8/04 |
| 2022/0372380 A1 * | 11/2022 | Park ........................ | B01J 35/1038 |

FOREIGN PATENT DOCUMENTS

| | | |
|---|---|---|
| CN | 101172237 A | 5/2008 |
| CN | 101992102 A | 3/2011 |
| EP | 3 733 820 A1 | 11/2020 |
| JP | 64-33105 A | 2/1989 |
| JP | 5-287012 A | 11/1993 |
| JP | 2005-146054 A | 6/2005 |
| KR | 2002-0024713 A | 4/2002 |
| KR | 10-0366972 B1 | 1/2003 |
| KR | 10-2009-0031916 A | 3/2009 |
| KR | 10-2010-0100834 A | 9/2010 |
| WO | 96/01691 A1 | 1/1996 |

OTHER PUBLICATIONS

International Searching Authoirty, International Search Report dated Apr. 5, 2019 in International Application No. PCT/KR2018/016310.

\* cited by examiner

*Primary Examiner* — Irina Krylova
(74) *Attorney, Agent, or Firm* — Sughrue Mion, PLLC

(57) ABSTRACT

Provided are a hydrogenation reaction catalyst and a preparation method therefor, and more particularly, to a hydrogenation reaction catalyst including sulfur as a promoter, thereby selectively hydrogenating an olefin by changing a relative hydrogenation rate of the olefin and an aromatic group during a hydrogenation reaction of an unsaturated hydrocarbon compound containing an aromatic group, and a preparation method therefor.

9 Claims, 1 Drawing Sheet

HYDROGENATION REACTION CATALYST AND PREPARATION METHOD THEREFOR

CROSS REFERENCE TO RELATED APPLICATIONS

This application is a National Stage of International Application No. PCT/KR2018/016310, filed on Dec. 20, 2018, claiming priority based on Korean Patent Application No. 10-2017-0183458, filed on Dec. 29, 2017.

TECHNICAL FIELD

The present invention relates to a hydrogenation reaction catalyst and a preparation method therefor, and more particularly, to a hydrogenation reaction catalyst including sulfur as a promoter, thereby selectively hydrogenating an olefin by changing a relative hydrogenation rate of the olefin and an aromatic group during a hydrogenation reaction of an unsaturated hydrocarbon compound containing an aromatic group, and a preparation method therefor.

BACKGROUND ART

Lower olefins (i.e. ethylene, propylene, butylene and butadiene) and aromatic compounds (i.e. benzene, toluene, and xylene) are basic intermediates widely used in the petrochemical and chemical industries. Thermal cracking or steam pyrolysis is a main type of process for forming these materials typically in the presence of steam and in the absence of oxygen. A feedstock may include petroleum gas and distillate, such as naphtha, kerosene, and gas oil. At this time, naphtha and the like may be thermally decomposed to produce light hydrocarbons including ethylene, propylene, C4 fractions (including butane, and butadiene), cracked gasoline (including benzene, toluene, and xylene), cracked kerosene (C9+ oil), cracked heavy oil (ethylene bottom oil), and hydrogen gas, and petroleum resin may be prepared by polymerization from oil or the like.

However, since the petroleum resin partially contains unsaturated bonds, the quality of the petroleum resin may be deteriorated. At this time, when a hydrogenation process of adding hydrogen is conducted, unsaturated bonds are removed to make a color brighter and a peculiar smell of petroleum resin is reduced, resulting in improvement in quality. In addition, since the petroleum resin, from which the unsaturated bonds are removed, is colorless and transparent, it is called a water-white resin. Such a petroleum resin is distributed as a high-quality resin with excellent heat and ultraviolet (UV) stability.

Petroleum resin copolymerized with C5 and C9 fractions and dicyclopentadiene (DCPD) is characterized in that the compatibility with a styrene-based polymer such as ethylene-vinyl acetate (EVA), styrene-isoprene-styrene (SIS), and styrene-butadiene-styrene (SBS) is controlled according to the aromatic content. Therefore, in the hydrogenation reaction of the petroleum resin, it is necessary to selectively hydrogenate the olefin of the resin so as to control the aromatic content and make the petroleum resin into the water-white resin.

Therefore, various catalysts have been studied to hydrogenate unsaturated petroleum resin feedstocks. In particular, in order to selectively hydrogenate an olefin from an aromatic unsaturated hydrocarbon, it is known to use a noble metal catalyst such as palladium (Pd) or platinum (Pt). The palladium catalyst is used as a selective hydrogenation reaction catalyst because of its excellent activity and selectivity as compared with other metal catalysts. However, a palladium-based catalyst has a problem that, when hydrogenation is performed in the presence of a liquid phase, palladium is lost and a Pd complex compound is formed. In addition, when a Ni-based catalyst is used, aromatic group is hydrogenated together, making it difficult to use the Ni-based catalyst for a selective hydrogenation reaction of an unsaturated hydrocarbon containing an aromatic group.

In order to solve these problems, U.S. Pat. No. 5,223,470 discloses a nickel catalyst containing sulfur supported on an alumina ($Al_2O_3$) carrier. However, the nickel catalyst is not a catalyst for aromatic/olefin selective hydrogenation and does not contain copper. Hence, the nickel catalyst has different components from those of the present invention. U.S. Pat. No. 4,328,090 discloses a Ni—W catalyst containing sulfur supported on $\gamma$-$Al_2O_3$ or a Ni—Mo catalyst containing sulfur as a catalyst for hydrogenating petroleum resin. However, the Ni—W catalyst or the Ni—Mo catalyst is not a catalyst for aromatic/olefin selective hydrogenation. Also, the Ni—W catalyst or the Ni—Mo catalyst is different from the present invention because the catalyst of the present invention does not contain tungsten (W) or molybdenum (Mo). U.S. Pat. No. 3,687,989 discloses a catalyst containing $Ni_3S_2$, $WS_2$, and $MoS_2$ for fat or fatty acid hydrogenation. Only olefin hydrogenation is disclosed and the catalyst is not used for aromatic/olefin selective hydrogenation. Also, the components of the catalyst are different from those of the present invention.

Furthermore, much research has been conducted into hydrogenation reaction catalysts in which an active metal is supported on silica, alumina, or activated carbon.

Korean Patent Laid-Open Publication No. 10-2010-0100834 discloses the use of a catalyst containing nickel and sulfur for selective hydrogenation. However, Korean Patent Laid-Open Publication No. 10-2010-0100834 does not disclose the type of carrier, the powder form of carrier, and the use of sulfur as an accelerator. Japanese Patent Laid-Open Publication No. H10-0502865 discloses a hydrogenation reaction catalyst in which nickel and sulfur are supported on a silica or alumina carrier. However, Japanese Patent Laid-Open Publication No. H10-0502865 does not disclose the inclusion of sulfur as an accelerator, the powder form, and the aromatic/olefin selective hydrogenation.

Accordingly, the inventors of the present application have studied to develop a nickel catalyst containing copper and sulfur as a promoter. While solving the problem of aromatic/olefin selective hydrogenation that has not been solved in the above documents, a catalyst can be prepared through a simple process. A hydrogenation method having high aromatic/olefin hydrogenation selectivity when applying the prepared catalyst to a hydrogenation reaction of an unsaturated hydrocarbon compound containing an aromatic group has been established. Furthermore, a water-white resin can be easily secured by using the catalyst developed as described above.

DESCRIPTION OF EMBODIMENTS

Technical Problem

The present invention has been made in an effort to solve the above-described problems.

An object of the present invention is to provide a hydrogenation reaction catalyst including sulfur as a promoter, thereby selectively hydrogenating an olefin by changing a relative hydrogenation rate of the olefin and an aromatic group during a hydrogenation reaction of an unsaturated hydrocarbon compound containing an aromatic group, and a preparation method therefor.

Another object of the present invention is to provide a hydrogenation reaction catalyst capable of controlling an aromatic content of an unsaturated hydrocarbon containing an aromatic group by selectively hydrogenating olefin, and a preparation method therefor.

Still another object of the present invention is to provide a hydrogenation reaction catalyst capable of easily manufacturing the water-white resin by controlling an aromatic content during a hydrogenation reaction of an unsaturated hydrocarbon compound containing an aromatic group, and a preparation method therefor.

Solution to Problem

In order to achieve the above-described objects of the present invention and achieve the characteristic effects of the present invention described below, the characteristic construction of the present invention is as follows.

A hydrogenation reaction catalyst according to the present invention includes nickel, a promoter, and a carrier, wherein the promoter includes copper and sulfur, the carrier is at least one selected from silica and alumina, and the nickel has an average crystal size of 1 nm to 10 nm and the hydrogenation reaction catalyst has an average particle size of 1 μm to 20 μm.

A content of the nickel may be in a range of 40 parts by weight to 80 parts by weight based on 100 parts by weight of a total composition, and a content of the copper may be in a range of 0.1 parts by weight to 5 parts by weight based on 100 parts by weight of the total composition. A mole ratio of the sulfur to the nickel may be in a range of 0.02:1 to 0.2:1.

A hydrogen adsorption amount per weight of the nickel may be in a range of 0.01 mmol-$H_2$/g-Ni to 0.5 mmol-$H_2$/g-Ni.

A method for preparing a hydrogenation reaction catalyst according to the present invention includes: producing a primary solution by dissolving nickel, copper compound, and a carrier powder in distilled water; adding the primary solution to a precipitation vessel and stirring and heating the primary solution to 50° C. to 120° C.; producing a secondary solution by injecting a solution containing a pH regulator and sulfur into the heated primary solution for 30 minutes to 2 hours, and forming a precipitate on which Ni is supported through precipitation; producing a dried product by washing, filtering, and heating the precipitate at 100° C. to 200° C. for 5 hours to 24 hours; and producing a reduced product by reducing the dried product in a hydrogen atmosphere at a temperature of 200° C. to 500° C.

The method may further include calcining the dried product in an air atmosphere at a temperature of 200° C. to 500° C. before the reduction in the hydrogen atmosphere.

The method may further include producing a powder catalyst by passivating the reduced product with a nitrogen mixed gas containing 0.1% to 20% oxygen.

The precipitation may be performed at a pH of 7 to 9.

A hydrogenation method is characterized by selectively hydrogenating an olefin of an unsaturated hydrocarbon compound containing an aromatic group by using the hydrogenation reaction catalyst prepared according to the present invention.

A selectively hydrogenated petroleum resin prepared by the hydrogenation method may have an APHA value of 30 or less.

Advantageous Effects of Disclosure

A hydrogenation reaction catalyst and a preparation method therefor according to the present invention have an effect that can selectively hydrogenate an olefin by greatly decreasing a relative hydrogenation rate of an aromatic group with respect to the olefin when conducting a hydrogenation reaction of an unsaturated hydrocarbon compound containing an aromatic group by including sulfur as a promoter.

The present invention has an effect that can control the aromatic content of the unsaturated hydrocarbon compound containing the aromatic group by selectively hydrogenating the olefin.

Furthermore, the present invention has an effect that can easily manufacture a water-white resin by controlling an aromatic content during a hydrogenation reaction of a petroleum resin

BEST MODE

Figure 1:
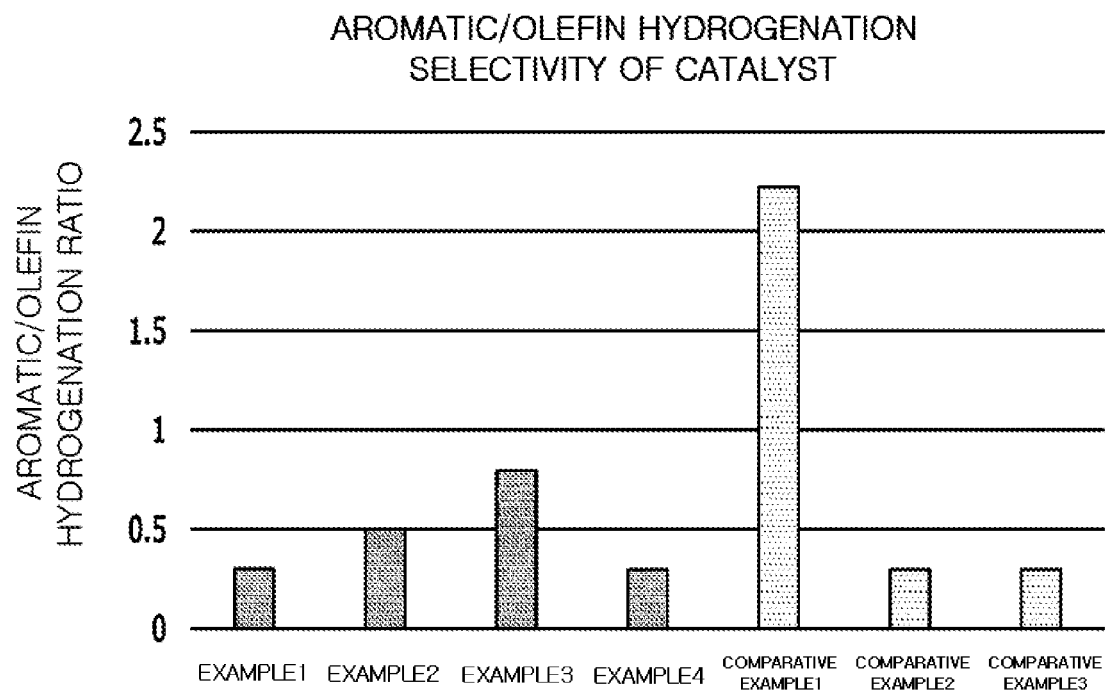
FIG. 1 is a graph showing aromatic/olefin hydrogenation selectivity of Examples and Comparative Examples.

The present invention will be described with reference to specific embodiments and the accompanying drawings. The embodiments will be described in detail in such a manner that the present invention may be carried out by those of ordinary skill in the art. It should be understood that various embodiments of the present invention are different, but need not be mutually exclusive. For example, certain shapes, structures, and features described herein may be implemented in other embodiments without departing from the spirit and scope of the present invention in connection with one embodiment. In addition, it should be understood that the locations or arrangement of individual components in the embodiments can be changed without departing from the spirit and scope of the present invention. Therefore, the following detailed description is not to be taken in a limiting sense, and the scope of the present invention is to be limited only by the appended claims and the entire scope of equivalents thereof, if properly explained. In the drawings, similar reference numerals refer to the same or similar functions throughout various aspects.

Hereinafter, embodiments of the present invention will be described with reference to the accompanying drawings, so that those of ordinary skill in the art can easily carry out the present invention.

A hydrogenation reaction catalyst according to the present invention includes nickel, a promoter, and a carrier. The promoter includes copper and sulfur. The carrier is at least one selected from silica and alumina. The nickel has an average crystal size of 1 nm to 10 nm, and more preferably 3 nm to 7 nm. When the average crystal size of the nickel is out of the above range, the activity of the catalyst may be deteriorated. In addition, the catalyst according to the present invention may have an average particle size of 1 μm to 20 μm, and more preferably 3 μm to 10 μm. When the average particle size of the catalyst is less than the above range, the filterability of the catalyst may be insufficient, and when the average particle size of the catalyst exceeds the above range, the activity of the catalyst may be deteriorated.

The content of the nickel may be in a range of 40 parts by weight to 80 parts by weight, preferably 50 parts by weight to 70 parts by weight, and more preferably 55 parts by weight to 65 parts by weight based on 100 parts by weight of the total catalyst composition. When the content of the nickel is less than the above range, the activity of the catalyst may be deteriorated, and when the content of the nickel exceeds the above range, dispersibility may be lowered, thus reducing the activity of the catalyst.

The content of the copper may be in a range of 0.1 parts by weight to 5 parts by weight, preferably 0.2 parts by weight to 2 parts by weight, and more preferably 0.5 parts by weight to 1 parts by weight based on 100 parts by weight of the total catalyst composition. When the content of the cooper is less than the above range, the nickel reduction may be decreased to deteriorate the activity of the catalyst, and when the content of the copper exceeds the above range, the nickel ratio of the surface of the active metal may be decreased to deteriorate the activity of the catalyst.

The mole ratio of the sulfur to the nickel may be in a range of 0.02:1 to 0.2:1, preferably 0.04:1 to 0.15:1, and more preferably 0.05:1 to 0.1:1. When the content of the sulfur is less than the above range, the selectivity of the hydrogenation reaction catalyst may be deteriorated, and when the content of the sulfur exceeds the above range, the activity of the catalyst may be deteriorated.

A nickel source is a nickel chloride precursor including metal salts such as nitrate, acetate, sulfate, or chloride, and most preferably a nickel chloride precursor including chloride.

In addition, a copper precursor may use at least one selected from nitrate, acetate, sulfate, chloride, and hydroxide, and a sulfur precursor may use at least one selected from alkali metal sulfide, thiophene, and mercaptan.

In the hydrogenation reaction catalyst according to the present invention, a hydrogen adsorption amount per the weight of the nickel may be in a range of 0.01 mmol-$H_2$/g-Ni to 0.5 mmol-$H_2$/g-Ni.

In general, during the hydrogenation reaction, both the olefin and the aromatic group included in the unsaturated hydrocarbon compound containing the aromatic group may be hydrogenated through the catalytic reaction. Thus, the catalyst capable of selectively hydrogenating olefins is required for controlling the aromatic content in the petroleum resin. When a nickel-based catalyst is used, it is known that it is difficult to control the aromatic content of the petroleum resin because the aromatic group of the resin is hydrogenated together.

However, the selective hydrogenation reaction catalyst according to one embodiment of the present invention has an effect that can selectively hydrogenate the olefin by greatly decreasing a relative hydrogenation rate of the aromatic group with respect to the olefin when conducting the hydrogenation reaction of the unsaturated hydrocarbon compound containing the aromatic group by including sulfur as the promoter.

In the hydrogenation reaction catalyst according to one embodiment of the present invention, a nickel compound and a promoter are mixed in a solvent, a solid carrier is suspended therein so that the nickel and the promoter form a precipitate, and the precipitate is deposited on the carrier. The carrier may be at least one selected from silica ($SiO_2$) and alumina ($Al_2O_3$).

In addition, the hydrogenation reaction catalyst according to one embodiment of the present invention can hydrogenate the petroleum resin including C5 or C9 petroleum fractions, by-products, and combinations thereof through distillation, pretreatment, and polymerization.

In the hydrogenation reaction of the unsaturated hydrocarbon compound containing the aromatic group, the temperature may be 100° C. to 400° C., and preferably 200° C. to 300° C., and the pressure may be 1 bar to 200 bar, and preferably 30 bar to 100 bar. The hydrogenation time may be mainly changed according to the temperature, the amount of catalyst, and the degree of hydrogenation. The hydrogenation reaction may be performed in various reactors. Preferably, the hydrogenation reaction may be performed in a continuous stirred tank reactor (CSTR), a loop reactor, an autoclave reactor, or the like according to the mixing method.

A method for preparing a hydrogenation reaction catalyst according to the present invention includes: producing a primary solution by dissolving nickel, copper compound, and a carrier powder in distilled water; adding the primary solution to a precipitation vessel and stirring and heating the primary solution to 50° C. to 120° C.; producing a secondary solution by injecting a solution containing a pH regulator and sulfur into the heated primary solution for 30 minutes to 2 hours, and forming a precipitate on which Ni is supported through precipitation; producing a dried product by washing, filtering, and heating the precipitate at 100° C. to 200° C. for 5 hours to 24 hours; and producing a reduced product by reducing the dried product in a hydrogen atmosphere at a temperature of 200° C. to 500° C.

The method may further optionally include calcination of the dried product in an air atmosphere at a temperature of 200° C. to 500° C. before the reduced product was produced by reducing the dried product in the hydrogen atmosphere.

The method may further include producing a powder catalyst by passivating the reduced product with a nitrogen mixed gas containing 0.1% to 20% oxygen.

In addition, the optimal activity may be exhibited when the reduction temperature is 200° C. to 500° C., preferably 300° C. to 450° C., and more preferably 370° C. to 430° C., as described above.

In addition, the precipitation may be performed in an environment of pH 7 or higher by base addition or electrochemical means. Preferably, the precipitation may be performed at pH 7 to pH 9. At this time, a basic compound may be added for base addition, and a basic additive may include sodium carbonate, sodium hydroxide, sodium hydrogen carbonate, or a hydrate thereof. However, the present invention is not limited thereto. Preferably, the basic compound may include sodium carbonate or a hydrate thereof.

The catalyst according to the invention may be in the form of powders, particles, granules. Preferably, the catalyst according to the present invention may be in the form of powders.

The method for preparing the hydrogenation reaction catalyst according to the present invention can optimize the surface area, pore structure, and size according to the carrier. Since the content of nickel is high, the reduction can be performed even at a low temperature. The catalyst has excellent activity and can be uniformly dispersed. Furthermore, the side reaction between the nickel and the carrier can be suppressed.

A selective hydrogenation method is characterized in that olefin can be selectively hydrogenated by greatly decreasing a relative hydrogenation rate of an aromatic group with respect to olefin of an unsaturated hydrocarbon compound containing an aromatic group by using the nickel-supported catalyst including copper and sulfur as the promoter, which is prepared according to the present invention.

A hydrogenated petroleum resin prepared by the selective hydrogenation method has an APHA value of 30 or less.

An APHA color is also called Hazen scale or platinum-cobalt (Pt/Co) scale. The color of the hydrogenated petroleum resin is analyzed by the APHA value using the color standard analysis method (ASTM D1209), which is named after the American Public Health Association.

The standard is Platinum-Cobalt Stock Solution, which corresponds to APHA 500. The color is expressed by a numerical value subdivided in steps of 1 to 500 using a standard solution that is quantitatively diluted. D.I water used as a diluent corresponds to APHA 0. Since the APHA color is particularly correlated with yellowness index, the APHA color value of the measurement sample can be obtained by using the APHA color standard curve of the standard solution for yellowness.

The petroleum resin hydrogenated by the selective hydrogenation method of the present invention has an APHA value of 30 or less and an aromatic/olefin hydrogenation ratio of 0.1 to 1.0. Furthermore, the petroleum resin is a water-white resin in which the color and smell of the hydrogenated petroleum resin are almost disappeared.

MODE FOR INVENTION

Hereinafter, the structure and operation of the present invention will be described in more detail with reference to preferred examples of the present invention. However, these example are shown by way of illustration and should not be construed as limiting the present invention in any way.

Since contents not described herein can be sufficiently technically inferred by those of ordinary skill in the art, descriptions thereof will be omitted.

EXAMPLES

Example 1

50 ml of a solution, in which 1 g of porous silica powder having a surface area of 200 m$^2$/g and a pore size of 28 nm, nickel chloride (243 g/l nickel), and copper chloride (2.2 g/l copper) were dissolved in distilled water, was added to a precipitation vessel and then stirred and heated to 80° C. After reaching 80° C., 40 ml of a solution containing sodium carbonate (175 g/l) and sodium sulfide (15 g/l) was all injected within 1 hour by using a syringe pump, so that a sulfur/nickel mole ratio became 0.09. After the precipitation was completed, a pH of a slurry was 7.7. The slurry was washed and filtered with about 1.5 L of distilled water and then dried at 120° C. for 12 hours or more by using a drying oven. This was subdivided and then reduced at a temperature of 400° C. in a hydrogen atmosphere. After that, the reduced powder was passivated by using a nitrogen mixed gas containing 1% oxygen.

In the passivated catalyst, a content of nickel was 63.8% based on the weight of the catalyst, a content of copper was 0.87% based on the weight of the catalyst, a content of sulfur was 2.8% based on the weight of the catalyst, and an average size of the nickel crystals was measured to be 5.1 nm. The hydrogenation reaction for the activity test of the catalyst was carried out at a temperature of 230° C.

Example 2

40 ml of a solution containing sodium carbonate (175 g/l) and sodium sulfide (12.5 g/l) as a precipitating agent was all injected within 1 hour by using a syringe pump, so that a sulfur/nickel mole ratio of a hydrogenation reaction catalyst became 0.075. After the precipitation was completed, a pH of a slurry was 7.6. The remaining processes such as washing, filtering, and drying were carried out in the same manner as in Example 1.

In the passivated catalyst, a content of nickel was 62.1% based on the weight of the catalyst, a content of copper was 0.84% based on the weight of the catalyst, a content of sulfur was 2.5% based on the weight of the catalyst, and an average size of the nickel crystals was measured to be 5.0 nm. The hydrogenation reaction for the activity test of the catalyst was carried out at a temperature of 230° C.

Example 3

40 ml of a solution containing sodium carbonate (175 g/l) and sodium sulfide (10 g/l) as a precipitating agent was all injected within 1 hour by using a syringe pump, so that a sulfur/nickel mole ratio of a hydrogenation reaction catalyst became 0.06. After the precipitation was completed, a pH of a slurry was 7.7. The remaining processes such as washing, filtering, and drying were carried out in the same manner as in Example 1.

In the passivated catalyst, a content of nickel was 62.1% based on the weight of the catalyst, a content of copper was 0.86% based on the weight of the catalyst, a content of sulfur was 2.2% based on the weight of the catalyst, and an average size of the nickel crystals was measured to be 4.1 nm. The hydrogenation reaction for the activity test of the catalyst was carried out at a temperature of 230° C.

Example 4

A hydrogenation reaction catalyst was prepared in the same manner as in Example 1, except that a calcination step was included before the reduction in the hydrogen atmosphere. The calcination was carried out in a muffle box furnace. The dried powder was subdivided, heated to 400° C. in a condition of an air flow of 1,000 mL/min and a heating rate of 5° C./min, and then maintained for 3 hours. A recovery rate of the calcined powder was 80%. Subsequently, the obtained powder was subdivided and then reduced at a temperature of 400° C. in a hydrogen atmosphere. After that, the reduced powder was passivated by using a nitrogen mixed gas containing 1% oxygen. In the passivated catalyst, a content of nickel was 62.4% based on the weight of the catalyst, a content of copper was 0.85% based on the weight of the catalyst, a content of sulfur was 2.9% based on the weight of the catalyst, and an average size of the nickel crystals was measured to be 4.2 nm. The hydrogenation reaction for the activity test of the catalyst was carried out at a temperature of 230° C.

Comparative Example 1

In order to prepare a sulfur-free catalyst, precipitation, washing, filtering, drying, and reduction were sequentially carried out in the same manner as in Example 1 by using only a sodium carbonate solution excluding sodium sulfide in a precipitating agent.

50 ml of a solution, in which 1 g of porous silica powder having a surface area of 200 m$^2$/g and a pore size of 28 nm, nickel chloride (243 g/l nickel), and copper chloride (2.2 g/l copper) were dissolved in distilled water, was added to a precipitation vessel and then stirred and heated to 80° C. After reaching 80° C., 40 ml of a solution containing sodium carbonate (175 g/l) was all injected within 1 hour by using a syringe pump. After the precipitation was completed, a pH of a slurry was 7.8. The slurry was washed and filtered with about 1.5 L of distilled water and then dried at 120° C. for 12 hours or more by using a drying oven. After the dried powder was subdivided and reduced at a temperature of 400° C. in a hydrogen atmosphere, a hydrogenation reaction catalyst was prepared by the passivation of the reduced powder using a nitrogen mixed gas containing 1% oxygen.

In the passivated catalyst, a content of nickel was 63.2% based on the weight of the catalyst, a content of copper was 0.89% based on the weight of the catalyst, and an average size of the nickel crystals was measured to be 5.7 nm. The hydrogenation reaction for the activity test of the catalyst was carried out at a temperature of 230° C.

Comparative Example 2

A commercially available power-type catalyst in which 5 wt % of palladium was supported on a carbon support was purchased and used for selective hydrogenation. The catalyst has a powder form having an average size of 10 μm, a BET specific surface area of 1,190 m$^2$/g, and a total pore volume of 1.1 cm$^3$/g. The hydrogenation reaction for the activity test of the catalyst was carried out at a temperature of 230° C.

Comparative Example 3

An activity test of the catalyst was carried out by using the catalyst applied to Comparative Example 2. The hydrogenation reaction for the activity test was carried out at a temperature of 270° C.

Table 1 below shows the content of nickel (Ni) and the type and content of promoter in the catalyst compositions of Examples 1 to 4 and Comparative Examples 1 to 3.

TABLE 1

| | Ni/Si mole ratio | S/Ni mole ratio | Pd/C weight ratio | Hydrogen adsorption amount (mmol-H$_2$/g-Ni) |
|---|---|---|---|---|
| Example 1 | 3.2 | 0.09 | — | 0.020 |
| Example 2 | 3.2 | 0.075 | — | 0.041 |
| Example 3 | 3.1 | 0.06 | — | 0.087 |
| Example 4 | 3.1 | 0.09 | — | 0.023 |
| Comparative Example 1 | 3.2 | 0.00 | — | 0.982 |
| Comparative Example 2 | — | 0.00 | 0.05 | — |
| Comparative Example 3 | — | 0.00 | 0.05 | — |

<Test Example> Activity Test of Catalyst

A 300 ml autoclave including a hollow shaft stirrer and having a stirring speed of 1,600 rpm was used.

75 g of a solution in which 30 wt % of a non-hydrogenated petroleum resin was dissolved in Exxsol™ D40 was hydrogenated by adding 0.5% to 2% catalyst based on the mass of the petroleum resin at 230° C. and 90 bar, and the color was measured by ASTM D1209. The color (APHA value) of the petroleum resin, which was significantly proportional to the content of the olefin in the petroleum resin, was 750 before hydrogenation. When the color of the petroleum resin was 30 or less, the petroleum resin became a water-white resin with almost no color and odor of the petroleum resin. At this time, the remaining content of olefin (NMR % area) was less than 0.1%.

That is, when the hydrogenation reaction was carried out until the APHA value became 30 or less, almost no olefin remained. The amount of the aromatic group hydrogenated till that time was measured to compare aromatic/olefin hydrogenation selectivity. This value was measured to compare the catalytic activity. Results thereof are shown in Table 2 below.

TABLE 2

| | Reaction temperature (° C.) | Catalyst (kg-cat/kg-resin) | Aromatic/olefin hydrogenation ratio | APHA value of petroleum resin after hydrogenation |
|---|---|---|---|---|
| Example 1 | 230 | 0.02 | 0.3 | 23 |
| Example 2 | 230 | 0.02 | 0.5 | 18 |
| Example 3 | 230 | 0.02 | 0.8 | 20 |
| Example 4 | 230 | 0.02 | 0.3 | 15 |
| Comparative Example 1 | 230 | 0.01 | 2.2 | 21 |
| Comparative Example 2 | 230 | 0.001 | 0.3 | 49 |
| Comparative Example 3 | 270 | 0.001 | 0.3 | 16 |

Figure 2:
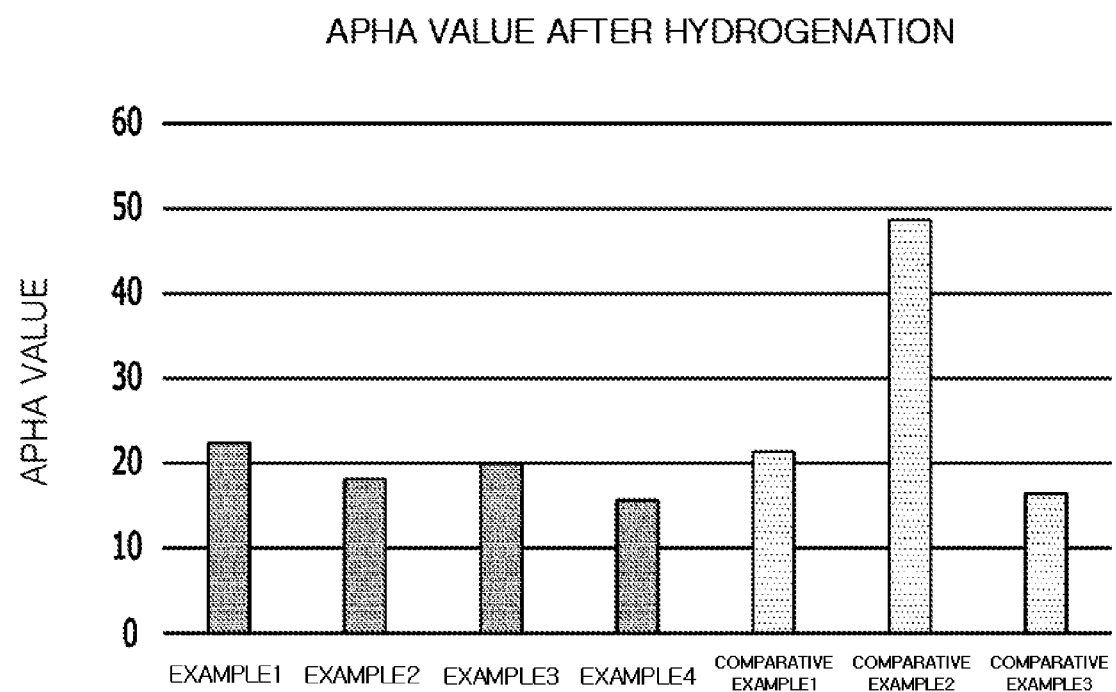
FIG. 2 is a graph showing APHA values of Examples and Comparative Examples after hydrogenation.

Referring to Table 2 and FIGS. 1 and 2, it is confirmed that Examples 1 to 4 in which sulfur is contained as the promoter have significantly excellent aromatic/olefin hydrogenation selectivity, as compared with Comparative Example 1. In addition, it is confirmed that the aromatic/olefin hydrogenation selectivity can be controlled through the content of sulfur added.

Furthermore, it is confirmed that Examples 1 to 4 prepared according to the present invention show equal or higher levels in the aromatic/olefin hydrogenation selectivity with the palladium catalysts of Comparative Examples 2 and 3, and in particular, the activation was well performed even at a lower temperature, as compared with Comparative Example 3.

In the hydrogenation reaction catalyst and the preparation method therefor according to the present invention, the olefin can be selectively hydrogenated by greatly decreasing a relative hydrogenation rate of an aromatic group with respect to olefin when conducting the hydrogenation reaction of the unsaturated hydrocarbon compound containing the aromatic group by including sulfur as the promoter.

In addition, according to the present invention, the aromatic content of the unsaturated hydrocarbon containing the aromatic group can be controlled by selectively hydrogenating the olefin.

Furthermore, according to the present invention, the water-white resin can be easily manufactured by controlling the aromatic content during the hydrogenation reaction of the unsaturated hydrocarbon compound containing the aromatic group.

While the present invention has been described by particular matters such as specific components and limited embodiments and drawings, this is provided only for helping the comprehensive understanding of the present invention. It will be understood by those of ordinary skill in the art that the present invention is not limited to the above-described embodiments and various modifications and variations can be made thereto without departing from the scope of the present invention.

Therefore, it will be understood that the spirit of the present invention should not be limited to the above-described embodiments and the claims and all equivalent modifications fall within the scope of the present invention.

The invention claimed is:

1. A hydrogenation reaction catalyst for petroleum resin; comprising nickel, a promoter, and a carrier,
wherein the promoter comprises copper and sulfur,
the carrier is at least one selected from the group consisting of silica and alumina,
the nickel has an average crystal size of 1 nm to 10 nm and the hydrogenation reaction catalyst has an average particle size of 1 μm to 20 μm,
a content of the nickel is in a range of 62 parts by weight to 65 parts by weight based on 100 parts by weight of the hydrogenation reaction catalyst,
a content of the copper is in a range of 0.8 parts by weight to 1 parts by weight based on 100 parts by weight of the hydrogenation reaction catalyst,
a mole ratio of the sulfur to the nickel is in a range of 0.02:1 to 0.2:1,
a content of the sulfur is in a range of 2.2 parts by weight to 2.9 parts by weight based on 100 parts by weight of the hydrogenation reaction catalyst,
the catalyst is to selectively hydrogenate an olefin by changing a relative hydrogenation rate of the olefin and an aromatic group during a hydrogenation reaction of an unsaturated hydrocarbon compound containing the aromatic group of the petroleum resin, and
the aromatic/olefin hydrogenation ratio is 0.3-0.8.

2. The hydrogenation reaction catalyst of claim 1, wherein a hydrogen adsorption amount per weight of the nickel is in a range of 0.01 mmol-$H_2$/g-Ni to 0.5 mmol-$H_2$/g-Ni.

3. A method for preparing the hydrogenation reaction catalyst according to claim 1, the method comprising:

(a) producing a primary solution by dissolving nickel, copper compound, and a carrier powder in distilled water;
(b) adding the primary solution to a precipitation vessel and stirring and heating the primary solution to 50° C. to 120° C.;
(c) producing a secondary solution by injecting a solution containing a pH regulator and sulfur into the heated primary solution for 30 minutes to 2 hours, and forming a precipitate on which Ni is supported through precipitation;
(d) producing a dried product by washing, filtering, and heating the precipitate at 100° C. to 200° C. for 5 hours to 24 hours; and
(e) producing a reduced product by reducing the dried product in a hydrogen atmosphere at a temperature of 200° C. to 500° C.

4. The method of claim 3, further comprising, in the step (d), calcining the dried product in an air atmosphere at a temperature of 200° C. to 500° C.

5. The method of claim 3, further comprising, in the step (e), producing a powder catalyst by passivating the reduced product with a nitrogen mixed gas containing 0.1% to 20% oxygen.

6. The method of claim 3, wherein the precipitation is performed at a pH of 7 to 9.

7. A hydrogenation method characterized by selectively hydrogenating an olefin of an unsaturated hydrocarbon compound containing an aromatic group by using the hydrogenation reaction catalyst prepared according to claim 3.

8. A selectively hydrogenated petroleum resin prepared by the hydrogenation method according to claim 7.

9. The selectively hydrogenated petroleum resin of claim 8, wherein the petroleum resin has an APHA value of 30 or less.

* * * * *